United States Patent [19]
Martin

[11] Patent Number: 5,300,040
[45] Date of Patent: Apr. 5, 1994

[54] SELF-LOCKING SAFETY SYRINGE
[75] Inventor: Robin Martin, McAllen, Tex.
[73] Assignee: Timothy A. Kershenstine, New Orleans, La.
[21] Appl. No.: 85,095
[22] Filed: Jul. 2, 1993

Related U.S. Application Data

[60] Division of Ser. No. 870,641, Apr. 16, 1992, Pat. No. 5,242,420, which is a continuation-in-part of Ser. No. 829,708, Feb. 3, 1992, Pat. No. 5,201,708.

[51] Int. Cl.⁵ .............................................. A61M 5/32
[52] U.S. Cl. ..................................... 604/198; 604/263
[58] Field of Search ............... 604/198, 192, 187, 110, 604/263

[56] References Cited
U.S. PATENT DOCUMENTS

| | | | |
|---|---|---|---|
| 4,923,447 | 5/1990 | Morgan | 604/198 |
| 5,201,720 | 4/1993 | Borgia et al. | 604/263 X |
| 5,242,416 | 9/1993 | Hutson | 604/198 X |

*Primary Examiner*—John D. Yasko
*Attorney, Agent, or Firm*—Keaty & Keaty

[57] ABSTRACT

The invention relates to a safety syringe to prevent accidental puncture of attending medical personnel by an infected syringe needle. The safety syringe has an elongated tubular casing which receives the needle guard in a telescopical relationship thereto. At least on locking tab attached to the exterior of the needle guard extends outwardly through an opening formed in the casing, such that depression of the locking tab allows telescopical movement of the needle guard inwardly into the casing. A tension member retains the needle guard in its fully extended position unless the tension of the member is overcome by compression of the needle guard during injection or the drawing of a medicine. The tension member can be in the form of a coil spring surrounding the syringe barrel and urging against the needle guard and the flange plate of the casing, or in the form of an elastic resilient member attached under tension between the needle guard and the casing.

5 Claims, 1 Drawing Sheet

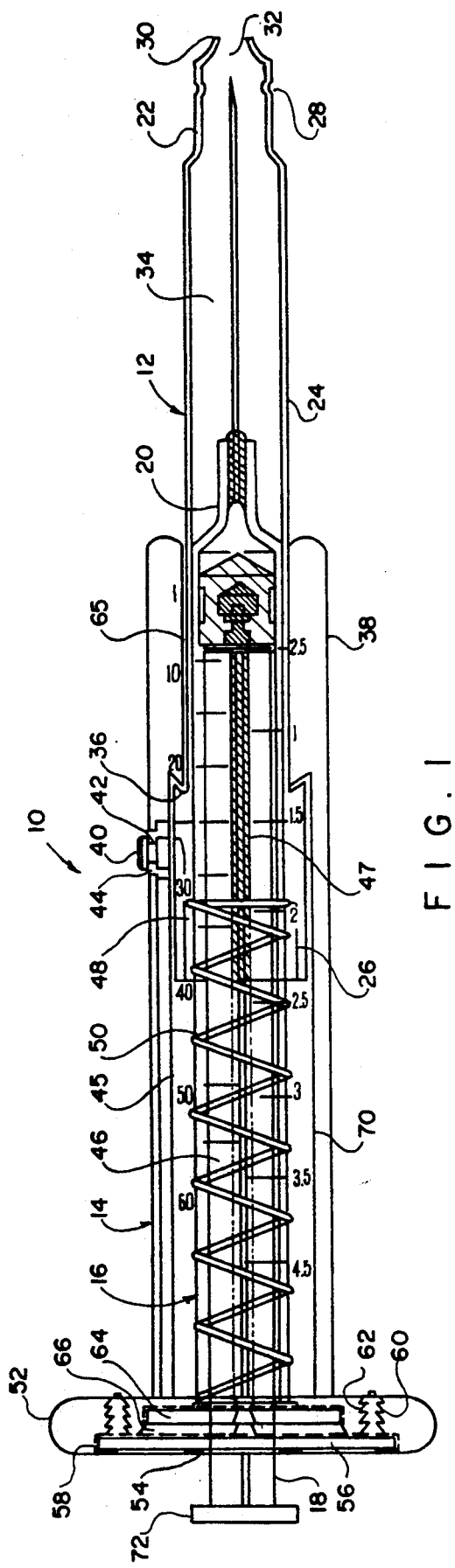
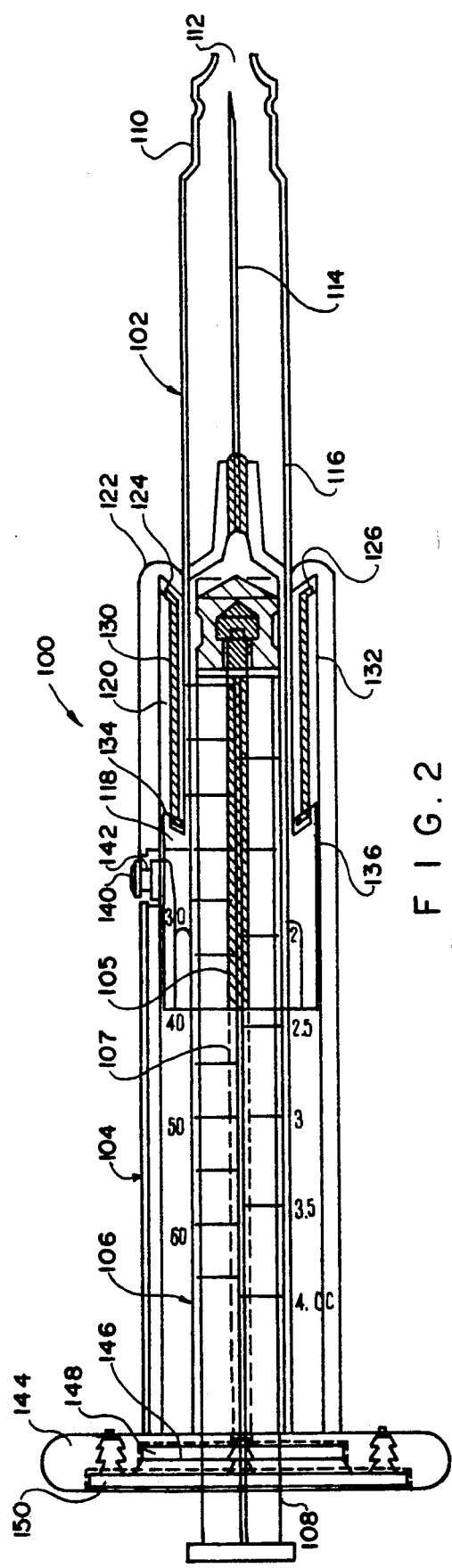

SELF-LOCKING SAFETY SYRINGE

CROSS-REFERENCE TO RELATED APPLICATIONS

This is a division of application of application Ser. No. 870,641, filed Apr. 16, 1992, now U.S. Pat. No. 5,242,420, which is a continuation-in-part of my co-pending application Ser. No. 829,708 filed on Feb. 3, 1992 now U.S. Pat. No. 5,201,708 and entitled "Self-Locking Safety Syringe", the disclosure of which is incorporated by reference herein.

BACKGROUND OF THE INVENTION

This invention relates to medical equipment, and more particularly to a safety syringe designed to prevent accidental needle stick injuries by medical personnel, particularly with respect to contaminated needles.

The ever increasing spread of diseases transmitted by blood and other bodily fluids, such as Acquired Immune Deficiency Syndrome and Hepatitis B, creates a real threat to medical personnel of accidental, inadvertent puncturing of the skin by a syringe needle, which has been in contact with an infected patient and transmittal of the often fatal disease to the unfortunate medical attendant. Despite educational programs carried by many hospitals, every day somewhere in the United States at least one nurse or a medical attendant, who comes into contact with an infected syringe needle, will become punctured by such needle, while trying to dispose of the used syringe, or during any other manipulation of dirty syringes.

Various attempts have been made to resolve this problem by proposing to use a protective syringe needle guard, which would cover the needle when the syringe is not in use and prevent the needle from being exposed during those times. However, such devices are expensive to manufacture, difficult to use, requiring several steps in preparing the syringe for utilization and, so far, have not found wide acceptance in the medical profession.

The present invention has a general objective of overcoming drawbacks and shortcomings associated with the prior art and provision of an inexpensive, easy to use self-locking safety syringe.

SUMMARY OF THE INVENTION

It is, therefore, an object of the present invention to provide a self-locking safety syringe which is designed to prevent exposure of the needle during routine handling by medical personnel.

It is another object of the present invention to provide a locking device for covering the needle, which is easy to use and inexpensive to manufacture.

It is a further object of the present invention to provide a needle guard which is equipped with means to prevent free rotation of the needle guard within a protective casing.

These and other objects of the present invention are received through the provision of a safety guard device for a syringe needle, which comprises an elongated casing having at least one opening formed in the body thereof, an elongated needle guard which is telescopically connected to the casing in co-axial alignment therewith and is adapted for movement between a first position, substantially covering a needle assembly of a syringe and a second position. A depressible locking tab is attached to the needle guard and extends through a co-aligned opening formed in the casing to lock the needle guard in its first position, when the syringe is not in use for performing of an injection or withdrawing of medicine from a medicine bottle.

A resilient elastic spring means continuously urges the needle guard to the first position, the tension of the spring means being overcome only by a double safety mechanism: by depressing the locking tab and exerting a pressure on a forward end of the needle guard, so as to move the needle guard inwardly into the casing and inject the needle. A syringe barrel, made to accept a ½ cc of liquid or more, is assembled in a co-aligned position with the needle guard and is fixedly attached at its outer end to a transverse flange of the casing.

To prevent misalignment of the locking tab in relation to a central axis of the needle guard and of the device, at least one runner is formed on the outer surface of the needle guard and a matching groove is formed in the inner wall of the casing to receive the runner in slidable engagement therein.

One end of the casing is closed by a transverse flange having a central opening therein. A plunger which carries a syringe piston on the innermost end is received through that opening in the transverse flange for movement within the syringe barrel and creation of a vacuum to allow drawing of medicine into the syringe.

BRIEF DESCRIPTION OF THE DRAWINGS

Reference will now be made to the drawings, wherein like parts are designated by like numerals, and wherein FIG. 1 is a schematic plan view of the device in accordance with the present invention utilizing a coil spring as a spring means.

FIG. 2 is a schematic plan view of the second embodiment of the device in accordance with the present invention, wherein a resilient flexible expandable band is used as a spring means to retain the needle guard in its first position.

DETAILED DESCRIPTION OF THE PREFERRED EMBODIMENT

Referring now to the drawings in more detail, numeral 10 designates the device of the present invention of FIG. 1. The device 10 comprises a needle guard 12, a barrel casing 14, a syringe barrel 16, a plunger 18, and a needle assembly 20.

The needle guard 12 comprises a first, nose portion 22, a second, middle portion 24, and a third, inner portion 26. As can be seen in the drawings, the second portion 24 is of a greater overall diameter than the nose portion 22, while the portion 26 is still of a greater diameter than the middle portion 24.

The nose portion 22 is provided with an annular groove 28 which is adapted for engaging an inner outwardly extending annular ridge formed on the interior of the medication bottle, when the nose portion 22 is inserted within the bottle neck. When used in drawing of medicine from other medication bottles, which are not equipped with the inner ridge, the nose portion 22 is adapted to contact the bottle neck on the exterior thereof by a forwardmost end 30 of the portion 22.

The needle guard 12 is formed substantially hollow and receives a syringe barrel 16 with an associated needle assembly 20 therein. A central opening 32 formed in the nose portion 22 to allow a needle 34 to pass therethrough during an injection or drawing of medication.

The middle portion 24 of the needle guard 12 is telescopically received within a part of the hollow casing 14, extending outwardly from the casing 14 to completely cover the needle assembly 20 when the syringe 10 is not in use.

An outwardly extending angularly inclined inner shoulder 36 is formed on the middle portion 24 at an area of connection between the portion 24 and an integrally formed portion 26. A matchingly inclined inwardly extending shoulder 38 is formed in the body of the casing 14 to match the angle of inclination of the shoulder 36. The shoulders 36 and 38 abut each other and prevent disengagement of the needle guard 12 from with the casing 14.

Integrally formed on an exterior wall of the middle portion 26 is a locking tab 40 which is supported on the wall by a support member 42. The locking tab 40 extends through an opening 44 formed in the thickness of the casing 14 to a distance slightly above the plane of the outer wall of the casing 14. The support member has a spring-like qualities, allowing to depress the locking tab 40, when necessary. However, once the tab is released, the support member 42 will "spring back" to its original position and force the locking tab 40 through the opening 44.

As will be appreciated, it is impossible to move the needle guard 12 forwardly or inwardly when the locking tab 40 is in the position shown in FIG. 1. However, when the locking tab 40 is depressed by the user's finger to recede into the opening 44 and align the top of the locking tab 40 with the interior wall of the casing 14, a respective movement between the needle guard 12 and the casing 14 is permitted.

The locking tab 40 is formed from a resilient material which has inherent properties of returning to its original condition. Such material can be a plastic, and the entire needle guard 12 can be manufactured from that material.

The interior wall of the casing 14 is provided with a locking tab groove 45, within which the tab 40 can slide in a co-axial movement in relation to the axis of the device 10.

Formed at about 90 to the opening 44 is another groove 46 formed in the interior wall of the casing 14. The groove 46 is adapted to receive in a sliding movement and engage a runner 47 which is formed on the outer surface of the needle guard portion 26 and extends outwardly therefrom. Engagement of the runner within the groove 46 prevents misalignment of the locking tab 40 from the locking tab groove and insures that the locking tab 40 will always "spring out" through the opening 44 anytime the needle guard 12 is fully extended, such as when the device 10 is not in use.

The needle guard 12 is further provided with a transverse shoulder 48 which forms a contact surface against which a coil spring 50 urges. The tension spring means 50 is mounted in a surrounding relationship about the exterior of the syringe barrel 16, with the second end of the spring means 50 urging against an inner surface of a flange plate 52, as will be described in more detail hereinafter.

The tension spring means 50 insures that the needle guard 12 is continuously urged forward, covering the needle assembly 20 unless two safety mechanisms are overcome. The first mechanism is the locking tab 40, while the second mechanism is application of an inward pressure on the end 30 of the nose portion 22. Only when the two conditions are met, that is when the locking tab is depressed and the pressure is applied to the nose portion 22, the spring 50 can be moved into compression and allow movement of the needle guard 12 telescopically into the interior of the casing 14 to permit injection by the needle 34 or drawing of a medicine.

Mounted on the end of the casing 14 opposite the needle guard 12 is a flange plate 52 which is fixedly attached to the casing 14, or formed integrally therewith. The flange plate 52 is provided with an opening 54 through which the piston 18 extends.

A sealing plate 56 is "snapped" into a specially formed recess 58 in the flange 52, the sealing plate 56 being provided with a plurality of pins 60 which extend at a right angle to the sealing plate 56. The pins 60 are formed with angularly oriented projections 62 which "snap" into matching openings formed in the body of the flange plate 52. Those openings are formed with matching angular grooves, or cuts into which the pins 60 snap, without any possibility of disengagement.

An end plate 64 is formed on the end of the syringe barrel 16 and is received within an inner groove 66 formed on the interior surface of the flange 52. The end plate 64 also snaps into the groove 66 and thereby attaches the barrel 16 to the casing 14.

The piston 18 moves axially in a sliding movement within the barrel 16, the piston 18 carrying a piston sealing member 65 on its forwardmost end. The sealing member 65 is made of a size to tightly engage the interior walls of the barrel 16 and create vacuum for drawing of medicine from a medicine bottle. The sealing member 65 insures that no air is admitted into the needle 34 from the interior of the syringe barrel 16.

In operation, the user removes the device 10 from its sterile packaging, wherein the device 10 is kept in a locked position illustrated in FIG. 1, until it is ready to use. The nurse then compresses the tab 40 and moves the nose 22 in contact with a neck of a medication bottle. By slightly pushing against the force of the spring 50, the user allows the needle guard 12 to move inwardly, telescopically in relation to the casing 14 and allows the sharp needle 34 to puncture the cap of the medication bottle 28.

A continuous pressure on the flange 52 will cause the needle 34 to further penetrate into the interior of the medication bottle. During that time the tab 40 is fully compressed and travels within the locking tab groove 45 inside the casing 14. During that time the fingers of the user are positioned at the base of the syringe, so as not to accidentally cover the opening 44. The spring 50 is fully compressed, and the user operates the plunger 18 moving it outwardly from the syringe barrel to allow introduction of medication into the syringe barrel 16.

Once the necessary amount is withdrawn, which can be detected by the comparison with the measuring indicia 70, the user removes the safety syringe 10 from the medication vial taking care not to cover the opening 44. The spring 50 then forces the needle guard 12 outwardly, again covering the needle 34 and automatically locking the needle guard 12 in a first, extended position, such that the locking tab 40 extends through the opening 44.

When the user contacts the skin of the patient, so as to give an injection, he again compresses the locking tab 40 and by holding and pressing the casing 14 towards the skin of the patient, causes the needle guard 12 to move inwardly into the casing 14 and allows injection of the needle 34 into the patient.

Continuous pressure inward, while holding the casing 14, forces the needle 34 into the body tissue of the patient. The hands of the user are then reversed, as he prepares to operate the plunger 18 again. One hand holds the syringe at its base, while the user reaches up with the other hand and pulls back the plunger 18, aspirating to make sure that the needle 34 is not in the patient's blood vessel, and then proceeds by compressing the plunger 18 towards the barrel casing 14, holding a thumb on the plunger end plate 72, and the second and third fingers around the flange plate 52 of the barrel casing 14.

Once the injection of medication is accomplished by pushing the plunger 18 in the fashion described above, the user again pulls on the casing 14, withdrawing it from the patient, while simultaneously the spring 50 extends again and forces the needle guard 12 into a position completely covering the needle guard 34.

As will be appreciated, at no time does the needle 34 become exposed to the air, thus avoiding a possibility of puncturing the skin of the user with an infected needle.

Turning now to the embodiment of FIG. 2, an alternative resilient elastic spring means for use with the safety syringe needle of the present invention will be discussed. As can be seen in FIG. 2, the syringe needle 100, similarly to the syringe needle 10 is provided with a needle guard 102, a casing 104, a syringe barrel 106, and a plunger 108. The needle guard 102 is formed with a nose portion 110 which has a central opening 112 therein, through which a needle 114 travels during injection or drawing of a medicine.

The needle guard 102 has a middle portion 116 and a third, inner portion 118.

An interior chamber 120 is formed in the casing 104 adjacent a first end 122 thereof. A pair of securing members 124 and 126 are formed on the interior of the surface 104, each made in the form of an inwardly turned hook, to which one end of an elastic means 130 and 132, respectively is secured.

The elastic means 130 and 132 each can be made in the shape of an elongated flexible resilient band, made from such material as, for example, latex, or any other material having similar physical properties. It is necessary that the material from which the bands 130 and 132 are made be resilient and have an inherent property to return to its compressed state when not expanded, or stretched.

The second end of the tension members 130 and 132 is engaged by hook-shaped band securing members 134 and 136, respectively, formed on the exterior of the needle guard 102.

As can be seen in the drawings, the band securing members 134 and 136 curve inwardly from the middle portion 18 towards the center of the device 100. The tension bands 130 and 132 can be simply wrapped over the hooks 134 and 136 and retained therein.

As will be appreciated, the bands 130 and 132 are slightly stretched, so that in their tendency to return to their original size they will pull the needle guard 102 outwardly and forwardly from the casing 104. When the needle guard 102 is pushed into the casing 104 by engagement of the nose portion 110 either with the skin of the patient or the medication bottle, the bands 130 and 132 are allowed to slightly expand.

The bands 130 and 132, are made sufficiently narrow to prevent them from occupying too much space within the opening 120 and interfering with the smooth movement of the needle guard 102 within the syringe barrel 104.

Although the embodiment of FIG. 2 illustrates the use of a pair of bands 130 and 132, it will be appreciated that the number of the bands can be changed, as long as the equal force is applied to diametrically opposite sides of the needle guard 102 during use of the device 100.

The remainder of the structure of the device 100 is similar to the structure of the syringe 10, in that it provides for the use of one, or more locking tabs 140 extending through an opening 142 formed in the casing 104. Similarly, the attachment of the casing 104 with the flange plate 144 is accomplished by engagement of an end plate 146 of the syringe barrel 106 within a groove 148 of the flange 144. A sealing plate 150 is "snapped" into the corresponding groove formed in the outer surface of the flange plate 144 to seal that end of the device 100. A runner 105 and groove 107 arrangement is similarly made in the needle guard 102 and the casing 104, respectively, to ensure alignment of the locking tab 140 with the opening 142.

The operation of the device 100 is similar to the operation of the device 10 in all other respects, except that in this embodiment the abutting of runner 105 against the end of the runner groove 107 is the means for preventing disengagement of the needle guard 102 from the casing 104 and is also a means for correctly positioning the locking tab 140 in co-alignment with the opening 142 whenever the needle guard 102 is fully extended.

The devices 10 and 100 can be made from clear, transparent plastic, with the exception of the needles 34 and 114, which are made of metal. The spring 50 can be made from steel or other resiliently strong material, while the bands 130 and 132 can be made from other materials than latex.

Many other changes and modifications can be made within the design of the present invention without departing from the spirit thereof. I, therefore, pray that my rights to the present invention be limited only by the scope of the appended claims.

I claim:

1. A self-locking safety syringe device, comprising:
   an elongated tubular casing having a distant end and a hook-shaped securing member formed on the interior of the casing adjacent said distant end;
   a syringe barrel having a needle assembly affixed thereto said syringe barrel being securely attached to one end of the casing;
   an elongated hollow needle guard telescopically coaxially engaged with the casing, the needle guard being movable between a first position, substantially covering the needle assembly and a second, retracted position;
   a resilient depressible means for locking the needle guard in the first position, said locking means being carried by an exterior of the needle guard; and
   an elastic means for continuously urging the needle guard into the first position, to thereby prevent accidental movement of the needle guard into the second position even after the locking means has been depressed.

2. The device of claim 1, wherein said needle guard has an inner portion formed with a hook-shaped securing member.

3. The device of claim 2, wherein said elastic means is at least one elastic flexible band stretched under tension between the hook-shaped securing member of the casing and the hook-shaped securing member of the needle guard.

4. A self-locking safety syringe device, comprising:
   an elongated tubular casing;
   a syringe barrel having a needle assembly affixed thereto, said syringe barrel being securely attached to one end of the casing;
   an elongated hollow needle guard telescopically coaxially engaged with the casing, said needle guard being movable between a first position, substantially covering the needle assembly and a second, retracted position;
   a resilient depressible means for locking the needle guard in the first position, said locking means being carried by the needle guard and comprising at least one depressible locking tab fixedly attached to the needle guard and extending outwardly through a correspondingly aligned opening formed in the casing; and
   a tension spring means continuously urging the needle guard into the first position to thereby prevent accidental movement of the needle guard into the second position even after the locking means has been depressed, said tension spring means comprising at least one resilient elastic expandable member mounted between the needle guard and the casing.

5. The device of claim 4, wherein said casing has a distant end which is formed with at least one hook-shaped band securing member, and wherein said needle guard is formed with at least one hook-shaped securing member adjacent its inner end, and wherein said at least one resilient elastic expandable member is stretched under tension between said at least one band securing member of the casing and said at least one band securing member of the needle guard.

* * * * *